United States Patent [19]

Chandrasekaran et al.

[11] 4,060,084
[45] * Nov. 29, 1977

[54] METHOD AND THERAPEUTIC SYSTEM FOR PROVIDING CHEMOTHERAPY TRANSDERMALLY

[75] Inventors: Santosh Kumar Chandrasekaran; John Urquhart, both of Palo Alto; Jane Elizabeth Shaw, Atherton, all of Calif.

[73] Assignee: Alza Corporation, Palo Alto, Calif.

[*] Notice: The portion of the term of this patent subsequent to June 28, 1994, has been disclaimed.

[21] Appl. No.: 763,314

[22] Filed: Jan. 28, 1977

Related U.S. Application Data

[63] Continuation-in-part of Ser. No. 721,602, Sept. 7, 1976, Pat. No. 4,031,894, which is a continuation-in-part of Ser. No. 638,947, Dec. 8, 1975, abandoned, which is a continuation-in-part of Ser. No. 547,504, Feb. 6, 1975, abandoned.

[51] Int. Cl.² .................................. A61M 31/00
[52] U.S. Cl. .............................. 128/260; 428/28; 128/268
[58] Field of Search ............... 128/260, 268, 296, 155, 128/156, 130; 424/19, 20, 28, 65

[56] References Cited

U.S. PATENT DOCUMENTS

| | | | |
|---|---|---|---|
| 3,632,740 | 1/1972 | Robinson et al. | 424/28 |
| 3,731,683 | 5/1973 | Zaffaroni | 128/268 |
| 3,767,786 | 10/1973 | MacMillan | 424/65 |
| 3,783,869 | 1/1974 | Schnipper | 128/268 |
| 3,797,494 | 3/1974 | Zaffaroni | 128/268 |
| 3,849,238 | 11/1974 | Gould | 128/268 X |
| 3,993,073 | 11/1976 | Zaffaroni | 128/260 |
| 3,996,934 | 12/1976 | Zaffaroni | 128/268 |

OTHER PUBLICATIONS

"Scopolamine Permeation Through Skin en Vitro", S. K. Chandrasekaran, A. S. Michaels, P. S. Campbell & J. E. Shaw, *Journal Amer. Aust. Chem. Engr.,* , vol. 22, No. 5, pp. 828-832, Sept. 1976.

*Clinical Pharmacology & Therapeutics,* vol. 11, No. 5, Sept.-Oct. 1970, pp. 621-629, "A Theory of Motion Sickness Based On Pharmacological Reactions".

*Drug Permeation Through Human Skin:,* 37 Theory & in Vitro Experimental Measurement", Am. Inst. of Chem. Engr. Journal, vol. 21, No. 5, Authors: A. Michaels, A. Chandreaskaran, & J. E. Shaw, pp. 985-939, Sept. 1975.

*Primary Examiner*—Aldrich F. Medbery
*Attorney, Agent, or Firm*—Thomas E. Ciotti; Paul L. Sabatine; Edward L. Mandell

[57] ABSTRACT

Method and therapeutic system in the form of a bandage for providing chemotherapy transdermally by administering certain drugs to unbroken skin in an initial priming dose that quickly brings the systemic concentration of drug to a therapeutic level, followed by a substantially constant dosage that holds said level. The bandage is a four-layer laminate of, from the top: a protective backing; a drug reservoir lamina that is the source of the constant dosage; a microporous membrane that controls the constant dosage rate; and an adhesive layer that is the source of the priming dose and the means by which the bandage is attached to the skin.

10 Claims, 1 Drawing Figure

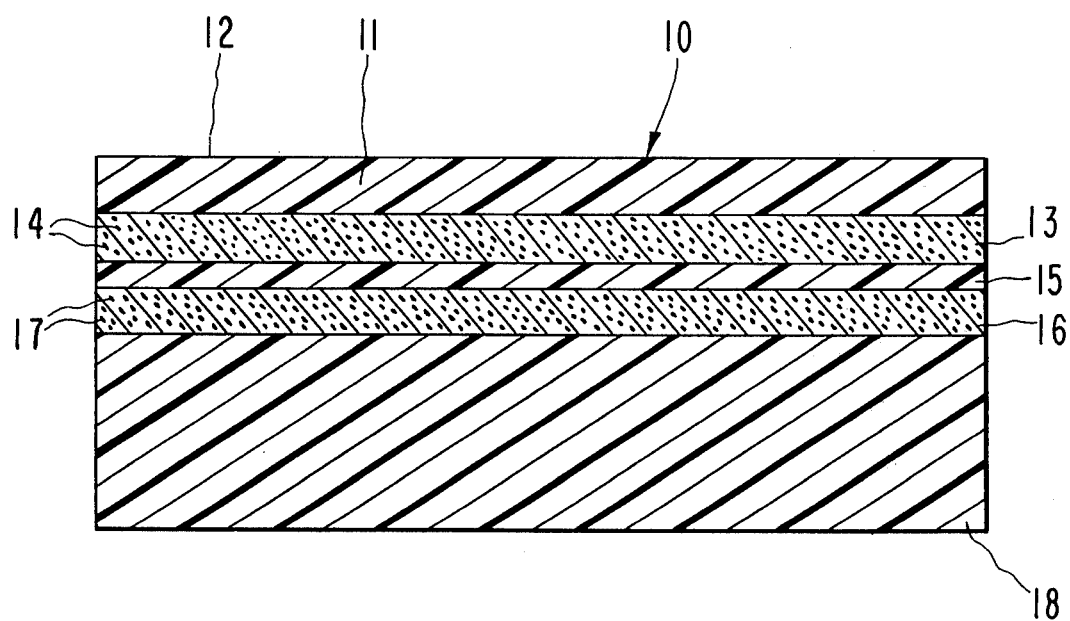

METHOD AND THERAPEUTIC SYSTEM FOR PROVIDING CHEMOTHERAPY TRANSDERMALLY

CROSS-REFERENCE TO RELATED APPLICATION

This application is a continuation-in-part of Ser. No. 721,602 filed Sept. 7, 1976, now U.S. Pat. No. 4,031,894 which in turn is a continuation-in-part of Ser. No. 638,947 filed 8 December 1975, now abandoned, which in turn is a continuation-in-part of Ser. No. 547,504 filed 6 February 1975, now abandoned.

BACKGROUND OF THE INVENTION

1. Field of the Invention

The invention is a method for providing chemotherapy transdermally and a therapeutic system in the form of a bandage structured specifically to carry out the method.

2. Description of the Prior Art

There are several patents that relate to bandages for administering systemic drugs transdermally. In this regard, U.S. Pat. No. 3,797,494 is believed to be the most relevant to the present invention. FIG. 2 of that patent shows a bandage that includes the basic elements of the invention bandage. Indeed, the invention bandage is considered to be a patentable embodiment of the bandage depicted in said FIG. 2. Both bandages are laminates that include a backing, a drug reservoir, a microporous membrane and a contact adhesive layer. However, the patented bandage is designed to administer drug at a constant rate; whereas the invention bandage is designed to administer drugs meeting certain criteria on a two phase program involving an initial or priming dose phase followed by a constant rate administration phase. In this regard, drug is present in the invention bandage in specific proportions in the contact adhesive layer as well as in the reservoir.

SUMMARY OF THE INVENTION

The invention is a method for providing chemotherapy transdermally for a predetermined prolonged time period comprising:

a. administering an initial or primary dose of a drug to a predetermined area of unbroken skin, said drug being (i) indicated systemically for said therapy at a predetermined systemic concentration (i.e. concentration in the blood) and (ii) capable of permeating through said predetermined area of skin at a rate that produces a steady-state systemic concentration of the drug at least about equal to said predetermined systemic concentration, with the proviso that the ratio of said rate on an hourly basis to the quantity of drug immobilized by said predetermined area of skin is less than about 10, wherein the quantity of the drug in the priming dose is at least a substantial portion of said quantity of drug immobilized by said predetermined area of skin; and b. thereafter continuing to administer the drug to said predetermined area of skin continuously at a rate that maintains the steady-state systemic concentration of the drug at about said predetermined systemic concentration.

The bandage for carrying out the above described method comprises a sandwich-type laminate comprising:

a. a drug reservoir lamina comprising:

i. a drug that is: indicated systemically for said therapy at a predetermined systemic concentration; and is capable of permeating through a predetermined area of unbroken skin at a rate that produces a steady-state concentration of the drug at least about equal to said predetermined systemic concentration, with the proviso that the ratio of said rate on an hourly basis to the quantity of drug immobilized by the predetermined area of skin is less than about 10, with the amount of the drug in the drug reservoir lamina being at least equal to the amount of drug calculated by multiplying the rate of drug permeation through said predetermined area of unbroken skin that produces a steady-state systemic concentration approximately equal to said predetermined systemic concentration times the predetermined prolonged time period; and ii. a carrier that is permeable to said drug;

b. a backing lamina that is substantially impermeable to the drug, one face of which forms the top of the bandage and the opposite face of which is adjacent to the top face of the drug reservoir lamina;

c. a microporous membrane lamina adjacent to the bottom face of the drug reservoir lamina through which the drug is released from the reservoir lamina after the bandage is affixed to said predetermined area of skin at approximately said rate that produces a steady-state systemic concentration approximately equal to said predetermined systemic concentration; and d. a contact adhesive lamina adjacent and below the microporous membrane lamina by which the bandage is affixed to the skin comprising:

i. a contact adhesive that is permeable to the drug; and ii. a priming dose of said drug, the quantity of drug in said priming dose being at least a substantial portion of the quantity of drug immobilized by said predetermined area of skin.

As used herein in connection with describing the invention method and the rate at which drug is released from said reservoir layer, the term "approximately" indicates that the rate may vary ±30%. Such variation may be inherent in the manufacturing procedure, or be caused by temperature fluctuation, poor affixation of the bandage to the skin, and the like. As used herein in connection with describing the magnitude of the priming dose the term "substantial" means at least about 50% and preferably at least about 75%.

BRIEF DESCRIPTION OF THE DRAWINGS

The drawing is an enlarged, schematic, cross-sectional view of an embodiment of the bandage of the invention.

DETAILED DESCRIPTION OF THE INVENTION

The method of the invention is useful for administering drugs that meet certain criteria. The first criterion is that the drug be indicated for systemic treatment of humans for the condition at hand. That is the drug must be known to be effective for such treatment. Such knowledge may be obtained from available literature concerning the pharmacology of the drug or from clinical testing of the drug for treating the condition. Correlatively, the systemic concentration at which the dug is effective for such treatment must be known. This concentration may be obtained from available literature or determined clinically by administering the drug intravenously or orally, observing the pharmacological effects of such administration and determining the drug level in the systemic fluids.

The second criterion for the drug is that it be capable of permeating through a predetermined area of skin not greater than about 10 cm² at a steady-state rate that produces a steady-state systemic concentration of drug that is equal to or greater than, preferably substantially greater than (i.e. at least 5 times as great), the minimum systemic concentration at which the drug is therapeutically effective. Determining this capability is a two-step exercise. Firstly, the steady-state rate at which the drug permeates human skin is measured. This may be done in vitro using known techniques, *Drug Permeation Through Human Skin: Theory and In Vitro Experimental Measurement,* Michaels, A., Chandrasekaran, K., Shaw, J., Am. Inst. of Chemical Eng. Journal, Vol. 21, No. 5, p. 985, 1975. Secondly, the rate found in the first step is compared with the intravenous or oral administration rates that yielded the systemic concentration of drug that was therapeutically effective. In the case of intravenous rates, the comparison is direct—on the assumption that all drug permeating through the skin is absorbed by the capillaries into systemic circulation. For oral rates the comparison is not direct since a portion of orally administered drug does not make it into systemic circulation (the effective oral dosage rates will be greater than the effective transdermal dosage rates). If the drug permeates through skin at a rate that produces a steady-state systemic concentration less than the therapeutically effective systemic concentration, the drug is simply not a candidate for effective transdermal administration. In this regard, it may be possible to increase the transdermal permeation rate to an acceptable level by pretreating or concurrently treating the skin with permeation enhancing agents. Thus, for the purposes of the invention said capability may be realized with or without such enhancers.

The third criterion is that the quantity of drug that permeates through a unit area of skin per hour be not less than about 1/10, preferably not less than about ¼, the quantity of drug that is immobilized per unit area of skin. If this criterion is not met the time period from the beginning of administration until the desired steady-state systemic concentration is reached will be unacceptably long. In this regard with many drugs the skin initially acts as a "sink" rather than as a "conduit", with most of the drug being immobilized or bound within the skin and not passing through to circulation. The quantity of drug that is immobilized per unit area of skin may be determined by known techniques, *Scopolamine Permeation Through Skin In Vitro,* Chandrasekaran, K., Michaels, A., Campbell, P., Shaw, J., Am. Inst. Chemical Eng. Journal, Vol. 22, No. 5, p. 828, 1976. Once the skin is "saturated", that is its immobilization sites are occupied with drug, it permits additional drug to pass through to circulation. The purpose of the priming dose of drug is to "saturate" the skin quickly and thereby shorten the time it takes for the drug to reach a steady-state therapeutic concentration in the body's systemic fluid. Thus the ideal amount of drug administered in the priming dose is a function of the immobilizing capacity and the area of the skin being treated and is approximately equal to the amount of drug immobilized by that area of skin. For instance with the drug scopolamine administered as an anti-nauseant/antiemetic, a priming dose of 50 to 150 mcg scopolamine per cm² of skin being treated will usually allow the therapeutic level in the plasma to be reached within about 2–3 hr. Accordingly, an adequate time margin of safety is provided if transdermal administration of scopolamine is begun at least about 3 hr before illness is expected. Alternatively the priming dose may be expressed in terms of the average release rate per unit area of skin over the first two hours of administration. Expressed in this manner the priming dose for scopolamine will be in the range of 20 to 60 mcg/hr/cm².

The purpose of the following continuous, prolonged, substantially constant rate administration portion of the method is to supplement, if necessary, the priming dose in delivering enough drug to reach the systemic concentration required to provide therapy and to hold that concentration at steady-state as long as is necessary, i.e. for as long as therepy is required. This rate may vary depending on the body weight (volume of systemic fluid) of the patient. In the case of scopolamine, in most instances the rate will be in the range of 5 to 15 mcg per hr for adults and 3 to 10 mcg per hr for children (measured as the average rate after 2 hr of administration, i.e. after the initial 2 hr of priming dose administration). In this regard in vitro permeation tests on scopolamine indicate it permeates skin at 3 to 30 mcg/cm² hr., depending on the particular skin involved.

The skin location at which the method is carried out is important for the reliability and reproducibility of the method. This is because the histology, thickness and vascularization of skin varies from individual to individual as well as from body site to body site on a given individual, and such variance may, and usually will, affect the efficacy with which drug is delivered to the plasma. Applicants have found that the effect of this variance may be substantially eliminated in either of two ways. The first way is to carry out the method at a skin site, namely the mastoidal area, where permeation of most drugs does not vary significantly from individual to individual and thus the quantity of drug delivered to the plasma or the rate at which such delivery is made is not significantly different between individuals. The second way is to eliminate the stratum corneum as a quantity-affecting or rate-affecting element by treating the skin at the administration site with a skin permeation enhancing agent. Such treatment will allow the method to be carried out at body sites, such as the arms, legs or torso, other than the mastoidal area. Depending on the particular agent involved, the treatment may occur prior to or concurrently with the administration of drug pursuant to the invention method. Likewise, the quantity of agent needed will depend on the particular agent used. In any event, the agent plays the dual role of increasing the permeability of the stratum corneum to drug and decreasing the tendency of the stratum corneum to immobilize drug. Examples of known agents which may be used are dodecyl pyrrolidone, dimethyl lauramide and dimethyl sulfoxide. All three of these agents may be used in pre-treatment applications. The pyrrolidone and lauramide may be applied to the administration site at about 4 to 8 mg/cm² for approximately an hour and then washed off or they may be administered simultaneously with the drug. The sulfoxide is preferably used only as a pretreatment at doses in the range of 5 to 100 mg/cm² for approximately one hour, and then washed off.

The drawing depicts a bandage, generally designated 10, that when applied to skin administers scopolamine base according to a priming dose-constant dosage program. Bandage 10 is a five-layer laminate. The top layer 11 is a backing that is substantially impermeable to scopolamine base. Its face 12 forms the top surface of the bandage. Backing 11 serves as a protective covering, keeps the volatile components of the bandage from escaping, and fulfills a support function. Preferably, backing layer 11 is itself a laminate of films of polymer and metal foil such as aluminum foil. Polymers that may be used in the layer are high and low density polyethylene, polypropylene, polyvinylchloride and polyethylene terephthalate.

Below and adjacent to layer 11 is a scopolamine reservoir layer 13. Layer 13 contains about 1 to about 6 mg scopolamine base, the undissolved portion of which is depicted as droplets 14. The scopolamine base contained in layer 13 is delivered to the plasma during the constant administration portion of the invention method. Droplets 14 are dispersed homogeneously in a gelled mixture of mineral oil of about 10 to about 100 cp at 25° C and a blend of polyisobutene. The oil will usually constitute 35% to 65% by weight of the mixture and the polyisobutene will correspondingly usually constitute 35% to 65% by weight of the mixture. The polyisobutene blend contains a low molecular weight polyisobutene (35,000–50,000 viscosity average molecular weight) and a high molecular weight polyisobutene (1,000,000–1,500,000 viscosity average molecular weight). Preferred mixtures comprise 35% to 65% mineral oil, 10% to 40% low molecular weight polyisobutene, and 20% to 40% high molecular weight polyisobutene. These oil-polyisobutene mixtures are excellent adhesives and help to hold the bandage together. If they were not good adhesives, other means, such as heat sealing, would have to be used to keep the bandage together.

The mineral oil in layer 13 functions as a carrier for the scopolamine base. Scopolamine base has limited solubility in the mineral oil (approximately 2 mg/ml) and the relative amounts of each in layer 13 are such that the mineral oil is saturated with the base for essentially the entire dispensing lifetime of the bandage.

The next lamina in the bandage is a microporous membrane 15 whose pores are filled with the above described mineral oil. Membrane 15 is the element of the bandage that controls the rate at which the base is released from layer 13. The flux of scopolamine through membrane 15 and the area of membrane 15 must be such that scopolamine is released from reservoir layer 13 to the skin at a substantially constant rate in the range of 5 to 15 mcg/hr (3 to 10 mcg/hr for children) after the bandage has been put in use. The flux follows Ficks' law. It is a function of the tortuosity, porosity and thickness of the membrane, the concentration gradient of scopolamine base across the membrane and the diffusion coefficient of scopolamine base in the mineral oil. The concentration gradient depends on the scopolamine concentrations in the mineral oil at the opposite sides of the membrane. The diffusion coefficient depends on the mineral oil viscosity and decreases with increasing viscosity. The three properties of the membrane are, of course, constant for any given membrane. Membranes that have porosities from about 0.1 to 0.85, tortuosities from 1 to 10, and thicknesses from $10 \times 10^{-4}$ to $10 \times 10^{-2}$ cm may be used. The membrane may be formed from polymers such as polypropylene, polycarbonates, polyvinylchloride, cellulose acetate, cellulose nitrate, and polyacrylonitrile.

Below and adjacent membrane 15 is a contact adhesive lamina 16. Lamina 16 contains 50 to 1500 mcg scopolamine base per cm² skin area. The undissolved portion of the scopolamine is depicted as droplets 17. The scopolamine base in lamina 16 is the priming dose of the invention method. The scopolamine is dispersed in the same mineral oil-polyisobutene mixture that is used in layer 13. Lamina 16 is the means by which the bandage is attached to the skin. In this regard the mineral oil-polyisobutene mixture adheres less strongly to skin than it does to the other laminas of the bandage; therefore, the bandage tends to remain intact when it is pulled off the skin.

Prior to use, the bandage also includes a strippable, protective coating 18 that covers lamina 16. Just prior to use, coating 18 is peeled away from lamina 16 and discarded. It may be made from scopolamine-mineral oil impermeable materials such as the polymers from which backing 11 may be made, with the provision that these materials are made strippable, such as by siliconizing.

Bandage 10 may be applied to either mastoidal region and it will administer scopolamine according to the described dosage program without requiring any prior or simultaneous treatment of the region with a skin permeation enhancing agent. As indicated above, if the bandage is applied to a body site other than a mastoidal area, the site should be treated with one or more of the described skin permeation enhancing agents. If simultaneous treatment is desired, the agent may be incorporated into bandage 10. In that instance, layers 13 and 16 will contain effective quantities of such agents.

The size of the bandage is not critical. The bandage will usually be sized to administer scopolamine to an area of skin in the range of 0.5 to 4 cm².

EXAMPLES

The following examples illustrate the invention. They are not intended to limit the scope of the invention in any way. Unless indicated otherwise, parts are by weight.

EXAMPLE 1

A solution of 29.2 parts high molecular weight polyisobutene (sold under the designation Vistanex MML-100, 1,200,000 viscosity average molecular weight), 36.5 parts low molecular weight polyisobutene (sold under the designation Vistanex LM-MS, 35,000 viscosity average molecular weight), 58.4 parts mineral oil (10 cp at 25° C), 15.7 parts scopolamine base and 860.2 parts chloroform is solvent cast onto an approximately 65 micron thick backing film of aluminized polyethylene terephthalate (sold under the designation MEDPAR) to form a scopolamine base reservoir layer approximately 50 microns thick. A contact adhesive layer-strippable coating combination is similarly prepared by solvent casting onto a 200 micron thick siliconized, aluminized, polyethylene backed polyethylene terephthalate film a solution of 31.8 parts of said high molecular weight polyisobutene, 39.8 parts of said low molecular weight polyisobutene, 63.6 parts of said mineral oil, 4.6 parts of scopolamine base and 860.2 parts chloroform. The resulting contact adhesive layer is approximately 50 microns thick.

The above described backing-reservoir layer combination is then laminated to one face of a 25 micron thick microporous polypropylene membrane (sold under the designation Celgard 2400) saturated with said mineral oil and the above described contact adhesive layer-strippable coating combination is laminated to the opposite face of the membrane. One cm² circular, disc-shaped bandages are punch cut from the resulting 5-layer laminate. Each bandage is designed to release an initial 150–250 mcg/cm² priming dose of scopolamine followed by an essentially constant dosage of 3–3.5 mcg/cm²/hr.

EXAMPLE 2

A solution of 22.3 parts of the high molecular weight polyisobutene described in Example 1, 28.0 parts of the low molecular weight polyisobutene described in Example 1, 44.9 parts mineral oil (66 cp at 25° C), 12.8 parts scopolamine base, 8.8 parts dimethyl lauramide and 883.2 parts of chloroform is solvent cast onto the backing film described in Example 1 to form a scopolamine base reservoir layer approximately 50 microns thick. A contact adhesive layer-strippable coating combination is similarly prepared by solvent casting onto the siliconized polyethylene terephthalate film described in Example 1 a solution of 23.5 parts of said high molecular weight polyisobutene, 29.5 parts of said low molecular weight polyisobutene, 47.6 parts mineral oil (66 cp at 25° C), 7.8 parts scopolamine base, 9.0 parts dimethyl lauramide and 882.6 parts chloroform. The resulting contact layer is approximately 50 microns thick.

The above-described backing-reservoir layer combination is then laminated to one face of a 25 micron thick microporous polypropylene membrane (sold under the designation Celgard 2400) saturated with said mineral oil and the above described contact adhesive layer-strippable coating combination is laminated to the opposite face of the membrane. Four cm² circular, disc-shaped bandages are punch cut from the resulting 5-layer laminate. Each bandage is designed to release an initial 125 mcg/cm² priming dose of scopolamine followed by an essentially constant dosage of 2 mcg/cm²/hr.

The bandages of Example 2 were tested on a double blind basis as follows. A bandage was applied to the skin behind the ear of 17 subjects prior to exposure to motion at sea. Placebo bandages (no scopolamine present) were similarly applied to 18 subjects. All subjects had a prior history of experiencing motion-induced nausea. Only one of the 17 subjects wearing the bandages of Example 2 1 became ill to the extent that additional antinauseant medication had to be administered while at sea. In contrast, 9 of the subjects wearing the placebo bandages had to receive additional antinauseant medication while at sea.

EXAMPLE 3

Therapeutic systems were made according to the procedure of Example 1 except that: the strippable coating was 127 micron thick siliconized polyethylene terephthalate film and the systems were each 2.5 cm² in area. In vitro tests of these systems showed they released an initial priming dose of approximately 200 mcg in the first two hours of use and an average of approximately 10 mcg/hr thereafter through 72 hr.

Modifications of the above described method and therapeutic systems that are obvious to persons of skill in the medical, chemical and/or pharmaceutical arts are intended to be within the scope of the following claims.

We claim:
1. Method for providing chemotherapy transdermally comprising:
   a. administering a priming dose of a drug to a predetermined area of unbroken skin, said drug being (i) indicated systemically for said therapy at a predetermined systemic concentration and (ii) capable of permeating through said predetermined area of skin at a rate that produces a steady-state systemic concentration of the drug at least about equal to said predetermined systemic concentration, with the proviso that the ratio of said rate on an hourly basis to the quantity of drug immobilized by said predetermined area of skin is less than about 10, wherein the quantity of the drug in the priming dose is at least a substantial portion of said quantity of drug immobilized by said predetermined area of skin; and
   b. thereafter administering the drug to said predetermined area of skin continuously at a rate that maintains the steady-state systemic concentration of the drug at about said predetermined systemic concentration.

2. The method of claim 1 wherein the skin is located at the mastoidal area.

3. The method of claim 1 wherein the drug is capable of permeating through said predetermined area of skin at a rate that produces a steady-state systemic concentration of the drug substantially greater than said predetermined systemic concentration.

4. The method of claim 1 wherein the quantity of drug in the priming dose is approximately equal to said quantity of drug immobilized by said predetermined area of skin.

5. The method of claim 1 wherein the skin is located at the mastoidal area, the drug is capable of permeating through said predetermined area of skin at a rate that produces a steady-state systemic concentration of the drug substantially greater than said predetermined systemic concentration, and the quantity of drug in the priming dose is approximately equal to said quantity of drug immobilized by said predetermined area of skin.

6. The method of claim 1 wherein said ratio is less than about 4.

7. The method of claim 1 wherein said predetermined area of skin is not greater than about 10 cm².

8. Therapeutic system in the form of a bandage for providing chemotherapy transdermally for a predetermined prolonged time period comprising a sandwich type laminate of:
   a. a drug reservoir lamina comprising:
      i. a drug that is: indicated systemically for said therapy at a predetermined systemic concentration; and is capable of permeating through a predetermined area of unbroken skin at a rate that produces a steady-state concentration of the drug at least about equal to said predetermined systemic concentration, with the proviso that the ratio of said rate on an hourly basis to the quantity of drug immobilized by the predetermined area of skin is less than about 10, with the amount of the drug in the drug reservoir lamina being at least equal to the amount of drug calculated by multiplying the rate of drug permeation through said predetermined area of unbroken skin that produces a steady-state systemic concentration approximately equal to said predetermined systemic concentration times the predetermined prolonged time period; and
      ii. a carrier that is permeable to said drug;

b. a backing lamina that is substantially impermeable to the drug, one face of which forms the top of the bandage and the opposite face of which is adjacent to the top face of the drug reservoir lamina;

c. a microporous membrane lamina adjacent to the bottom face of the drug reservoir lamina through which the drug is released from the reservoir lamina after the bandage is affixed to said predetermined area of skin at approximately said rate that produces a steady-state systemic concentration approximately equal to said predetermined systemic concentration; and d. a contact adhesive lamina adjacent and below the microporous membrane lamina by which the bandage is affixed to the skin comprising:
 i. a contact adhesive that is permeable to the drug; and
 ii a priming dose of said drug, the quantity of drug in said priming dose being at least a substantial portion of the quantity of drug immobilized by said predetermined area of skin.

9. The therapeutic system of claim 8 wherein the quantity of drug in the priming dose is approximately equal to the quantity of drug immobilized by said predetermined area of skin.

10. The therapeutic system of claim 8 wherein said ratio is less than about 4.

* * * * *